United States Patent [19]
Matthews et al.

[11] Patent Number: 5,559,436
[45] Date of Patent: Sep. 24, 1996

[54] METHOD AND APPARATUS FOR DISTINGUISHING SYNTHETIC DIAMONDS FROM NATURAL DIAMONDS

[75] Inventors: Marion Matthews, 8461 Vereda del Padre, Goleta, Calif. 93117; Charles R. Perry, Goleta, Calif.

[73] Assignee: Marion Matthews, Goleta, Calif.

[21] Appl. No.: 342,840

[22] Filed: Nov. 21, 1994

[51] Int. Cl.⁶ .......................... G01R 33/12; G01N 27/72
[52] U.S. Cl. .......................... 324/236; 324/234; 324/228
[58] Field of Search .................................. 324/228, 234, 324/236, 327, 377; 327/39–49; 356/30; 331/65

[56] References Cited

U.S. PATENT DOCUMENTS

| | | | |
|---|---|---|---|
| 3,808,524 | 4/1974 | Tarassoff et al. | 324/236 |
| 3,858,979 | 1/1975 | Elbe | 356/30 |
| 4,075,563 | 2/1978 | Battle | 324/236 |
| 4,125,770 | 11/1978 | Lang | 378/74 |
| 4,131,848 | 12/1978 | Battle | 324/236 |
| 4,255,962 | 3/1981 | Ashman | 73/15 A |
| 4,291,975 | 9/1981 | Raccah | 356/30 |
| 4,364,677 | 12/1982 | Ashman | 374/44 |
| 4,461,568 | 7/1984 | Welbourn et al. | 356/30 |
| 4,488,821 | 12/1984 | Wenckus | 374/44 |
| 4,523,467 | 6/1985 | Diederichs et al. | 73/573 |
| 4,616,939 | 10/1986 | Gitlis | 374/44 |
| 4,678,994 | 7/1987 | Davies | 324/234 |
| 4,835,471 | 5/1989 | Kutilin | 324/236 |
| 5,064,281 | 11/1991 | Davis | 356/30 |
| 5,143,212 | 9/1992 | Roberts et al. | 206/223 |

FOREIGN PATENT DOCUMENTS 617212  11/1926  France.

OTHER PUBLICATIONS

The Gemological, etc., J. Shigley, et al., 1986, pp. 192–208.
The Gemological, etc., J. Shigley, et al., 1987, pp. 187–206.
Determination of the Magnetic, etc., D. Gordon, Nov. 1958, pp. 929–934.
Are Synthetic Diamonds, etc., K. Nassau, pp. 29–32.
Synthetic Diamonds, etc., T. Chatham, 1993, pp. 1–4.
Gems & Gemology, 1994, pp. 123–124.
The Measurement of Magnetic, etc., J. Bruckshaw, et al., Dec. 1948, pp. 444–446.

*Primary Examiner*—Sandra L. O'Shea
*Assistant Examiner*—Jay M. Patidar
*Attorney, Agent, or Firm*—Darby & Darby, P.C.

[57] ABSTRACT

A counter is provided for measuring counting transitions of an oscillator having an inductor in a frequency determining circuit. The inductor is at least in part air-cored and has a port therein for admitting a sample diamond for testing. First, the oscillations are up counted over a precise time interval with no sample present, and then a sample diamond is placed into the pont to change the frequency of the circuit by an amount related to the quantity of ferromagnetic material in the sample diamond. Thereafter, a down count is performed for the oscillations with the sample diamond in place over a second time interval equal to the first interval. The difference in the up counts and the down counts is determined and displayed in a digital readout as a measure of the degree of likelihood of the sample being synthetic.

13 Claims, 10 Drawing Sheets

U6 (Y)

U6 (Y+D)

U2A (Q)

U2B (Q)

REF. CLOCK

METHOD AND APPARATUS FOR DISTINGUISHING SYNTHETIC DIAMONDS FROM NATURAL DIAMONDS

FIELD OF THE INVENTION

This invention relates to the screening of diamond gemstones so as to distinguish and detect synthetic diamonds from natural diamonds. More particularly, the invention relates to a method and apparatus for the rapid screening of diamond gemstones to determine the need for further investigation by identifying those likely to be synthetic. The invention produces a negative response for natural diamonds but reacts to the magnetic properties of synthetic diamonds to provide an indicator thereof.

BACKGROUND OF THE INVENTION

With the advent of gemstone quality synthetic diamonds the need has arisen for a rapid screening system available and affordable for the local jeweler to establish with reasonable probability whether a given diamond gemstone is natural or synthetic.

Existing systems for detection of synthetic diamond gemstones are summarized in the article Shigley et. al., "Sumitomo Synthetic Diamonds", *Gems and Gemology*, Winter 1986, pages 192–208. As there indicated the various properties of diamonds and particularly those that distinguish natural from synthetic stones are compared. Testing procedures were set forth which included color, (which may involve spectroscopy examination), fluorescence, electrical conductivity, thermal conductivity, specific gravity, microscope inspection, reaction to polarized light, and magnetism. As to the latter, magnetism, the test procedure involved gross attraction of the tested diamond to a magnet. However, it was found that only one of the tested synthetic diamonds was attracted so that the reliability of a test as there proposed was found inadequate.

A subsequently published article by Shigley et. al., "Gemological Properties of the De Beers Gem Quality Synthetic Diamonds", *Gems and Gemology*, Winter 1987, pages 187–206, repeated the previous work and investigation as applied to the De Beers synthetic diamond product. In addition to the tests earlier performed, the last publication also indicates that a test was conducted with catholuminescense and specific gravity investigations as well as chemical analysis of inclusions. As to the magnetic behavior it was noted that natural diamonds are only weakly magnetic if at all and that synthetic diamonds were believed to vary from strongly magnetic to non-magnetic. Accordingly, these studies concluded that magnetic investigation of synthetic diamond gemstones was not useful for identification. They further state that they foresaw difficulties in separating natural from synthetic colorless diamonds using any other conventional gemological technique.

The foregoing mentioned techniques that were proposed are all rather expensive and laborious to implement so that a need exists for a ready method and apparatus for screening synthetic gemstone diamonds from genuine diamonds.

SUMMARY OF THE INVENTION

In general, it is an object of the present invention to provide a method and apparatus for distinguishing synthetic diamonds from natural diamonds which will overcome the above limitations and disadvantages.

It is a further object of the invention to provide a method and apparatus of the above character based on a test for magnetic susceptibility of the stone.

It is known that natural diamonds exhibit very little if any magnetic behavior which could form the basis of their evaluation. However, synthetic diamonds have been found to contain magnetic inclusions inherent from the process from which they are made. Even though these inclusions can be quite small they are nevertheless found to exist in all synthetic diamonds that have been investigated whether or not detectable by the gross magnetic attraction methods mentioned in the literature. Even the clearest of synthetic stones contain ferrous material presumably more evenly distributed at the molecular level.

The present invention is predicated upon the realization that, given a suitably sensitive and appropriate instrumentation, it is possible to screen synthetic diamond gemstone from natural diamond gemstones by placing the stone under test into the core of an inductance in a linear oscillator circuit in which the magnetic character of the synthetic diamond changes the inductance and affects the frequency of the oscillating circuit in a way that a difference count can be obtained over a precisely repeatable interval for the condition of no sample present, compared to that when the sample is present, by an extremely sensitive but stable counting circuit. It is found that a reliable screening method can be based on this concept.

Generally, the invention provides a counter for measuring or counting transitions of an oscillator having an inductor in a frequency determining circuit. The inductor is in at least in part air cored, being wound around a core form having an opening therein for admitting a sample into the inductor core for testing. The method calls for up-counting the oscillations of the oscillator over a precisely repeatable time interval with no sample present and thereafter selectively placing an unknown sample diamond stone into coupled proximity or within the core of the inductor to change the oscillator frequency by an amount related to the ferromagnetic material contained therein. At that point the system is signaled to down-count the oscillations, subtracting the same from the up-count over a second time interval precisely equal to the first interval. The difference in counts is determined and displayed on a digital readout as a measure of the degree of likelihood that the sample under test is synthetic.

These and other features and objects of the invention will become apparent from the following description and claims, when taken with the accompanying drawings, of which:

DETAILED DESCRIPTION OF THE PREFERRED EMBODIMENTS

Figure 1:
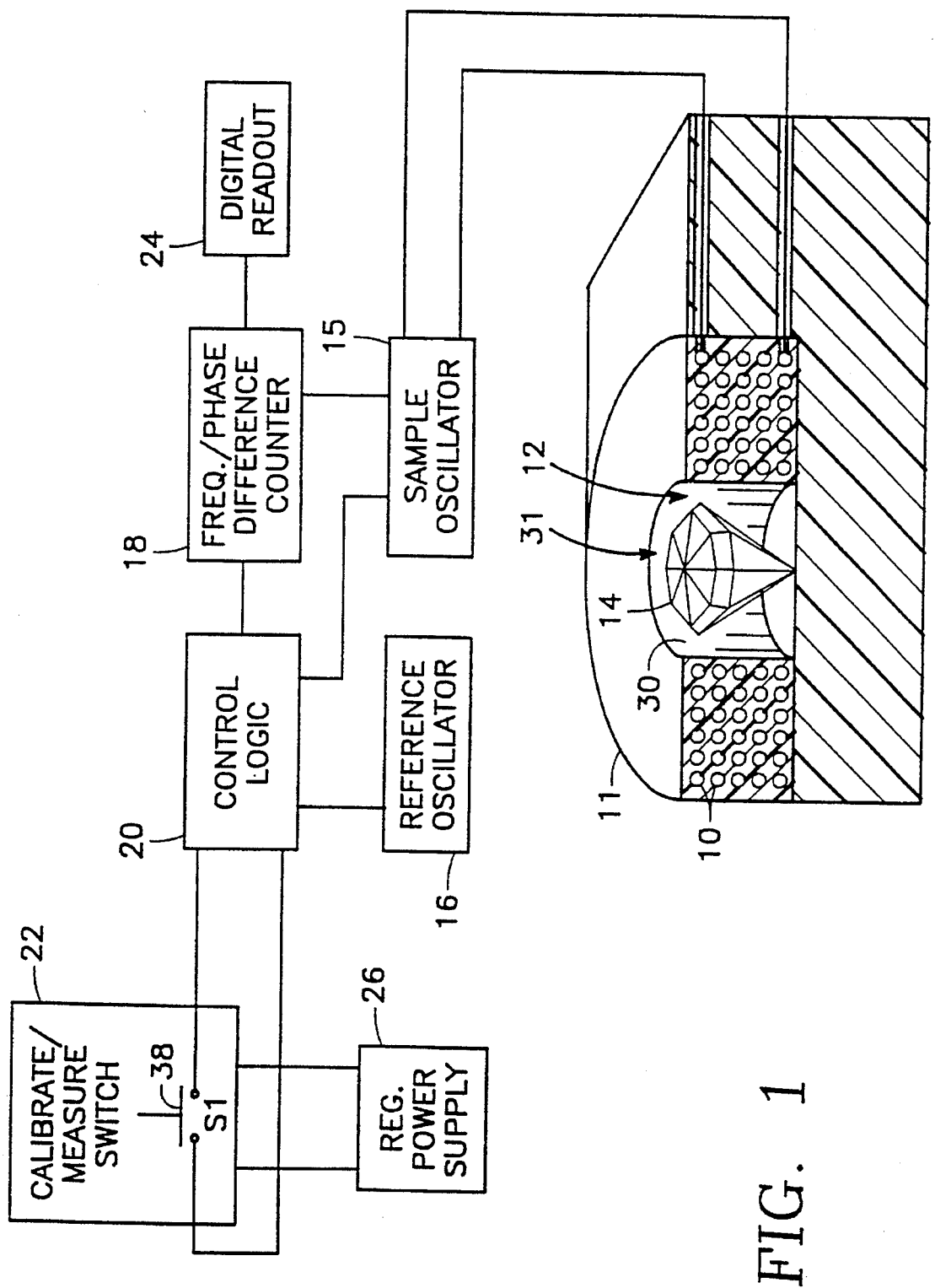
FIG. 1 is a block diagram of the detection apparatus constructed in accordance with the present invention.

Referring now to FIG. 1 there is shown a block diagram of apparatus of the invention which comprises a sample receiving coil 10 mounted with one end 12 opening through the top of a case into which the operator places the stone 14 to be tested. Coil 10 forms an inductance which is part of a frequency determining circuit configuration of a free-running sample oscillator 15.

A stable reference oscillator 16 clocks a counter 18 and control logic 20 controlled by a user calibrate/measure switch 22 to establish an up-count reference interval initiated by the operator before inserting the stone into coil 10. This interval is exactly matched after an unknown stone is placed for test and the operator gives the start test signal by releasing the switch 22.

During each of the reference interval and the test interval, the number of transitions of the sample oscillator is determined, and the down-counts of the latter are subtracted from the up-counts of the former to obtain a difference count which is displayed in a suitable readout. When the stone is natural, it contains no ferrous material, and the up-counts and down-counts match so that the output displayed is very low or zero. But, when the stone contains ferrous material, either in inclusions or distributed at the molecular level, the frequency of the sample oscillator is changed, so that the down-count will not equal the up-count. The difference of the counts is then displayed in digital readout 24 which signals the likelihood of a synthetic stone whenever the value exceeds a predetermined threshold level. The apparatus uses a stable voltage reference supplied by a regulated power supply 26 which can be connected to AC mains.

Sample Oscillator Circuit 15

Figure 2:
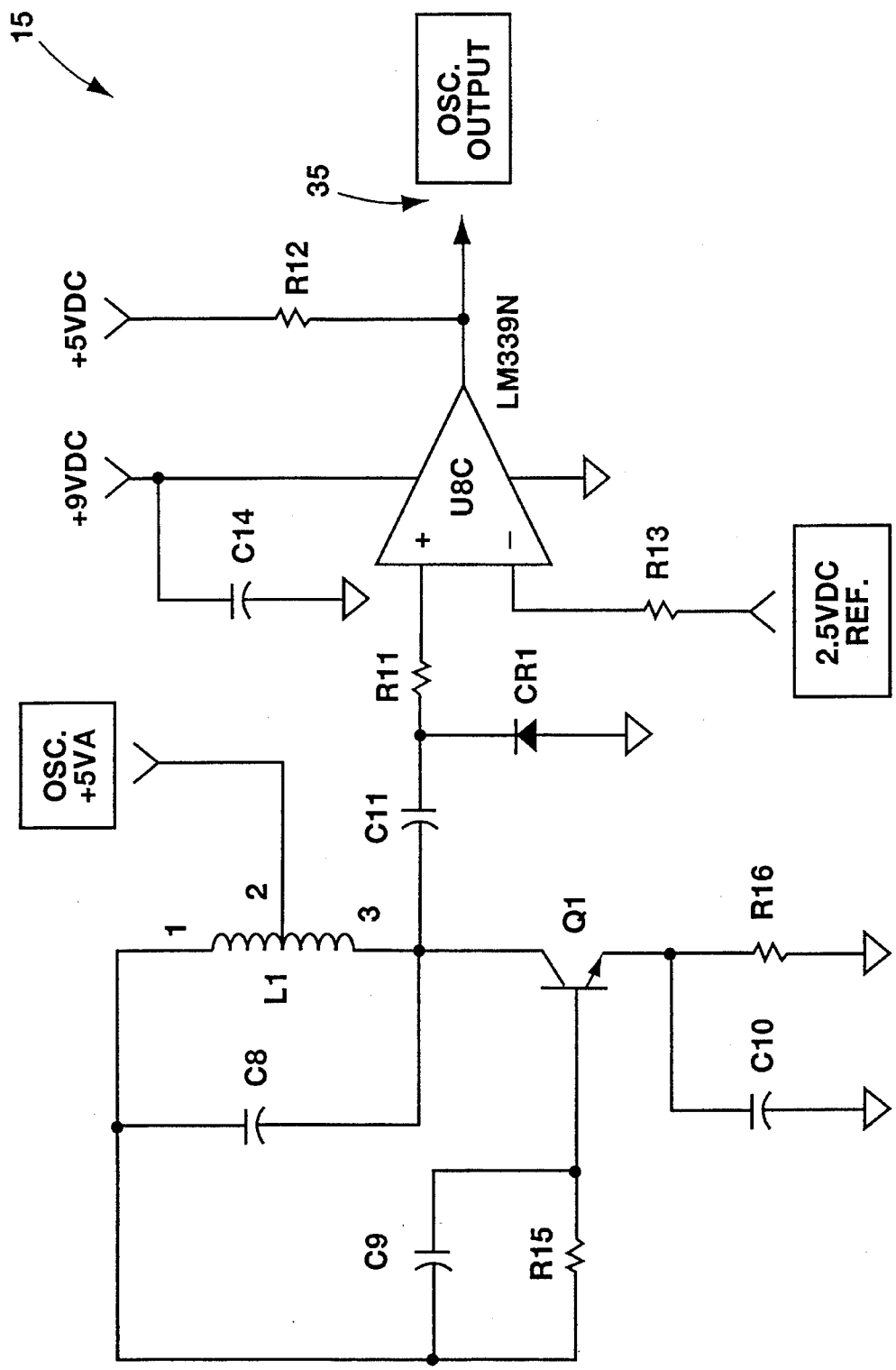
FIG. 2 is a detailed circuit diagram of the sample oscillator of FIG. 1.

Referring now to FIGS. 1 and 2, the sample oscillator is made up by coil 10 represented in the circuit diagram as inductor L1, transistor Q1, resistors R15 and R16 and capacitors C8, C9, C10 and C11 connected in a Hartley configuration. C8 and L1 determine the frequency of oscillation of the oscillator circuit.

Inductor L1 is of an open core form comprising a coil of wire wound on a hollow form 30 closed at the bottom, but open at the top to define a test chamber 31 into which the diamond to be tested is placed. The coil form opening 12 is circular, and of a diameter suitable for receiving a diamond of the size desired to test. A range of sizes can be tested with a form of a given opening. By was of example, an opening of from 7 to 9 millimeters can accommodate stones up to about 1.5 carats. The form opens upright so that the diamond stone to be tested may be dropped in from the top and removed by turning the tester case over. Alternatively, the stone can be temporarily attached to a strip of adhesive tape and lowered into the test chamber, or it can be inserted and removed with a pair of plastic tweezers.

The coil length is about ³⁄₁₀ths of an inch with the test chamber 31 contained within the coil length. While it is preferred that the stone be fully placed within the test chamber for reproducability of results, this is not critical. Nor is the portion of the stone within the coil and chamber; and, the stone may be placed either point end down or up.

The frequency of oscillation of the sample oscillator 15 changes when a synthetic diamond containing a small amount of ferrous material (typically iron and/or nickel) is placed in the test chamber 31 of the coil. The frequency does not significantly change when a natural diamond without any ferrous material is placed in the coil.

The output of the sample oscillator is isolated from the remainder of the detector circuits by integrated circuit U8C. This prevents the changing load at the OSC output from pulling the frequency of oscillation. The isolation circuit is made up of integrated circuit U8C, capacitor C14, resistors R11, R12 and R13. Diode CR1 prevents the input at integrated circuit U8C from going negative and being damaged.

The frequency of the sample oscillator is approximately 800 kHz. The diamond detector will function properly with an oscillator frequency of 100 kHz to 2 MHz. The frequency can be changed by changing the value of C8 or the number of turns of the coil 10 comprising L1. The output of the sample oscillator is a continuous sine wave signal appearing at the oscillator output 35.

Reference Oscillator 16

Figure 3:
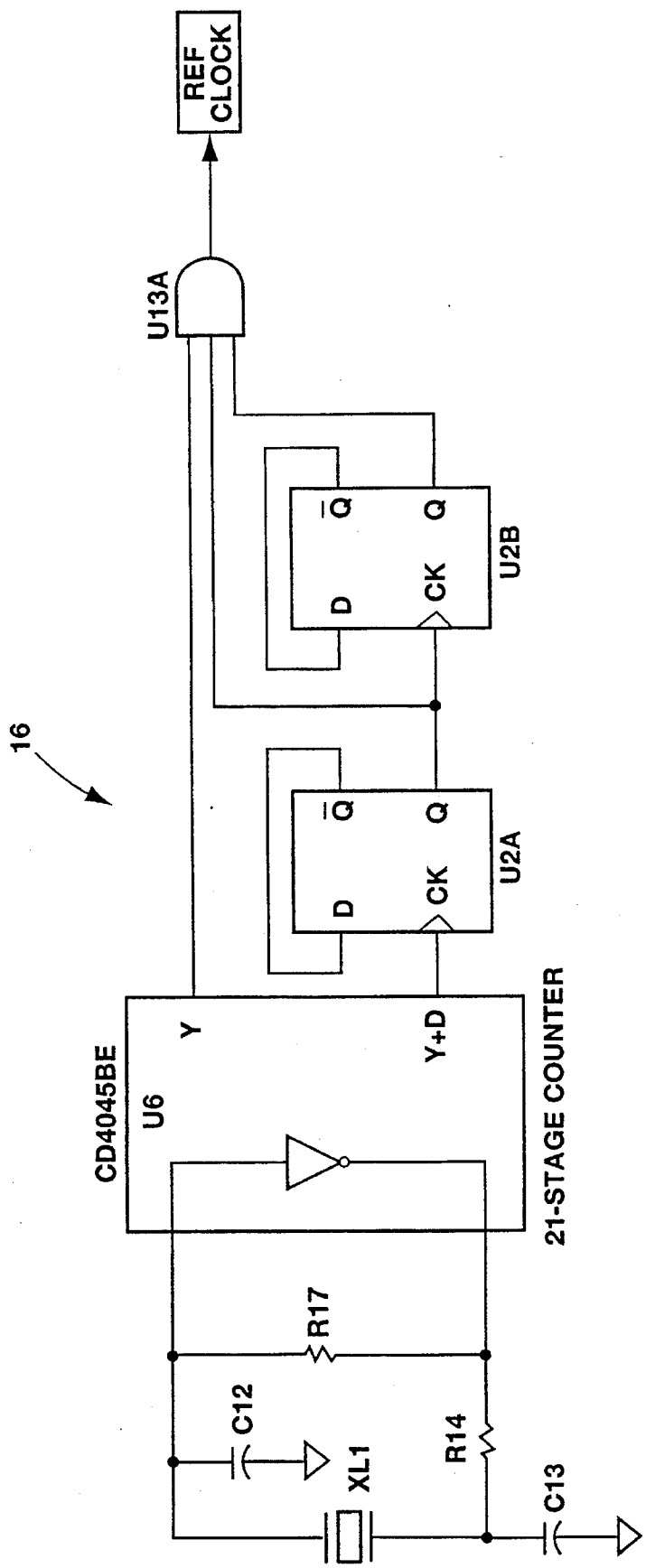
FIG. 3 is a detailed circuit diagram of the reference oscillator of FIG. 1.
Figure 4A:
FIG. 4A–4E is a set of timing signal graphs depicting the operation of the reference oscillator of FIG. 3.
Figure 4B:
Figure 4C:
Figure 4D:
Figure 4E:
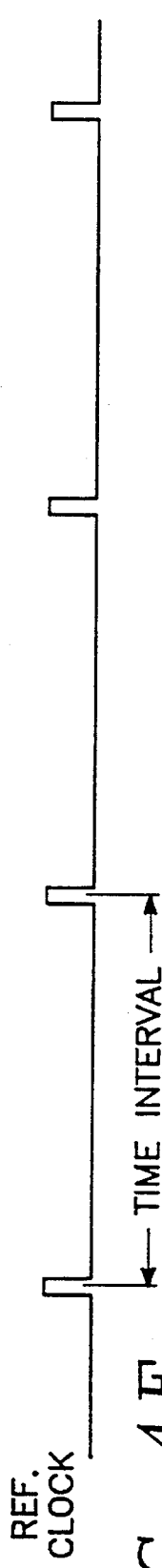

Referring now to FIGS. 1 and 3, the reference oscillator 16 provides a stable, accurate and repeatable time interval for the calibrate and measurement cycles. The calibration and measurement cycles time interval must be equal to a high degree of accuracy for the diamond detector of the invention to work properly.

The reference oscillator 16 includes a crystal XL1, integrated circuit U6, resistors R14 and R17 and capacitors C12 and C13 which together form a stable crystal controlled oscillator. The frequency of oscillation is set by X1.

The integrated circuit U6 also contains a 21 stage counter which divides the crystal oscillator circuit by 2,097,152. Integrated circuits U2A and U2B form two divide by 2 circuits.

AND gate U13A gates the output of the three divider circuits to form the required stable, accurate and repeatable time intervals. See FIG. 4 for the timing diagram of the reference oscillator 16.

The satisfactory time interval from the reference oscillator (at REF CLOCK) is approximately 4 seconds. The diamond test circuit will function properly with time intervals from approximately ½ second to 8 seconds. The time interval can be changed by changing the crystal X1.

Push to Test Switch Circuit 22

Figure 5:
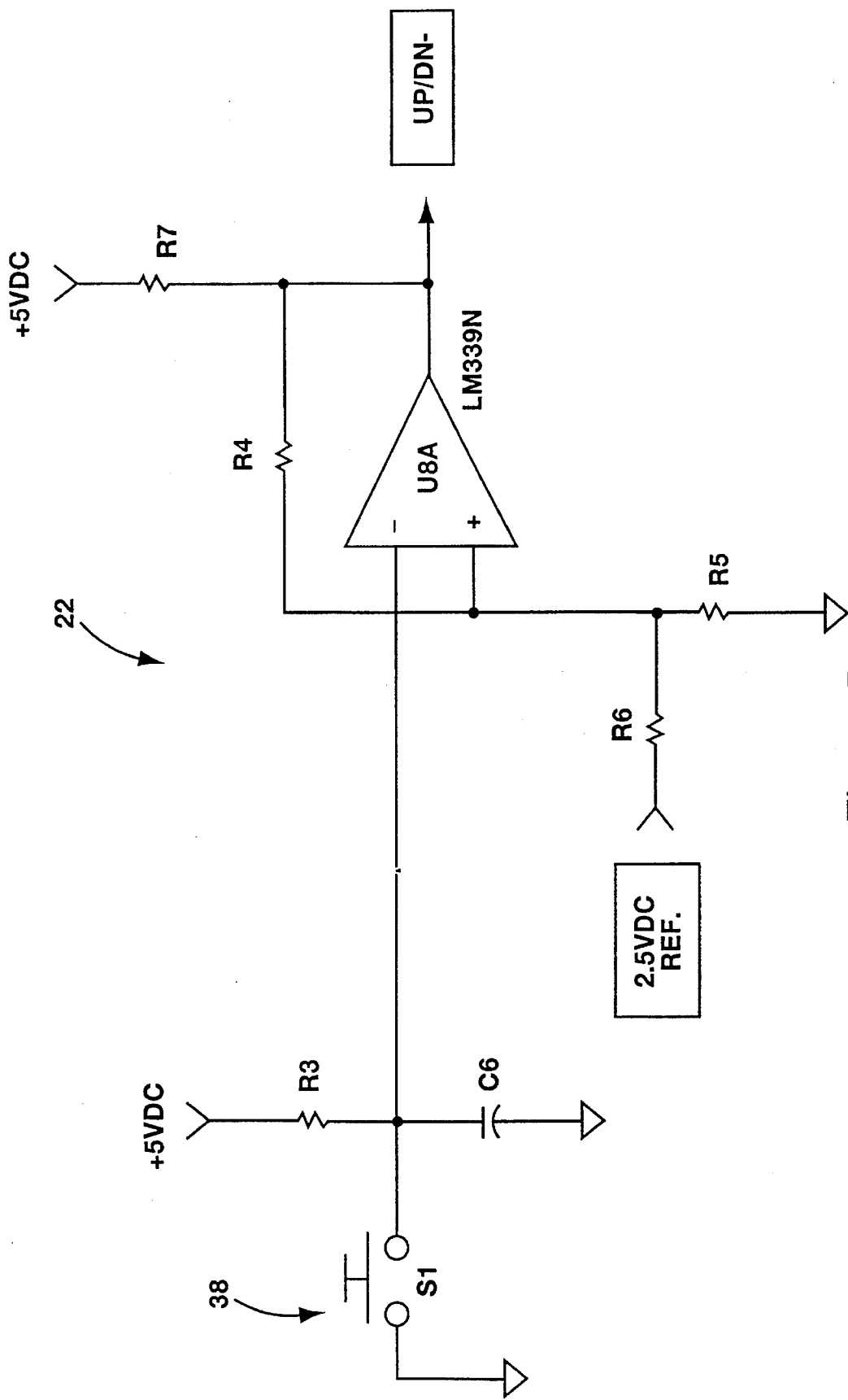
FIG. 5 is a detailed circuit diagram of the push to test circuit of FIG. 1.

Referring to FIGS. 1 and 5, the push to test circuit 22 includes a spring biased open switch S1 which controls the operation of the apparatus. When S1 is depressed, the output of integrated circuit U8A transitions to logic HI starting the up count or calibration cycle. When S1 is released the output of U8A transitions to logic LO starting the measurement cycle. Alternatively, S1 can be of a type that requires a second pressing to activate the second part of the cycle.

Resistor R3 is used to provide a logic HI at the (−) input to integrated circuit U8A when S1 is not depressed. Capacitor C6 along with the hysteresis circuit around integrated circuit U8A work together to eliminate S1 switch bounce when S1 is depressed or released. Resistors R4, R5 and R6 form the hysteresis circuit around U8A. Resistor R7 at the output of U8A is used to pull the output of U8A to logic HI when S1 is depressed, as U8A has an open collector output.

Control Logic 20

Figure 6:
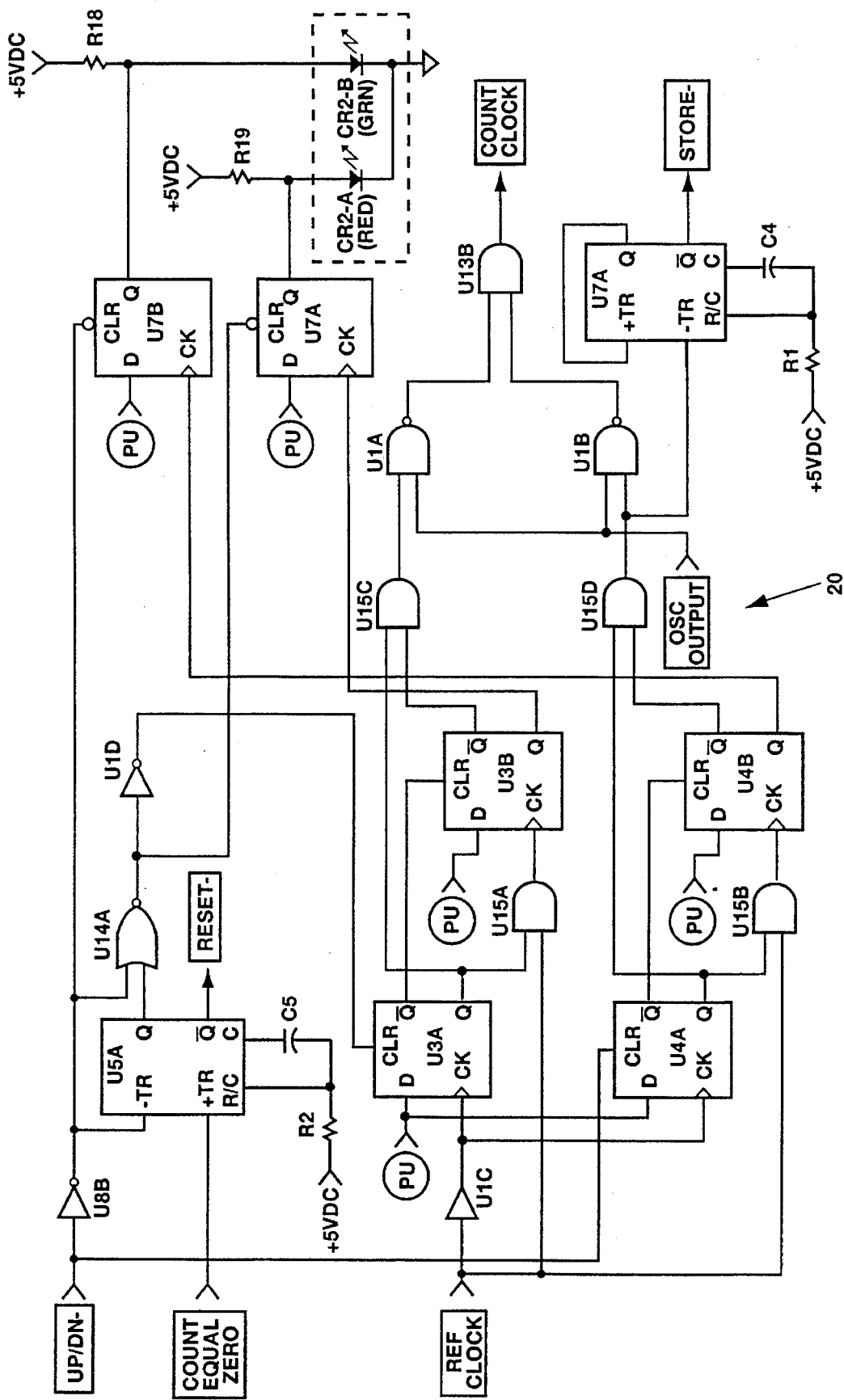
FIG. 6 is a detailed circuit diagram of the control logic circuits of FIG. 1.
Figure 7:
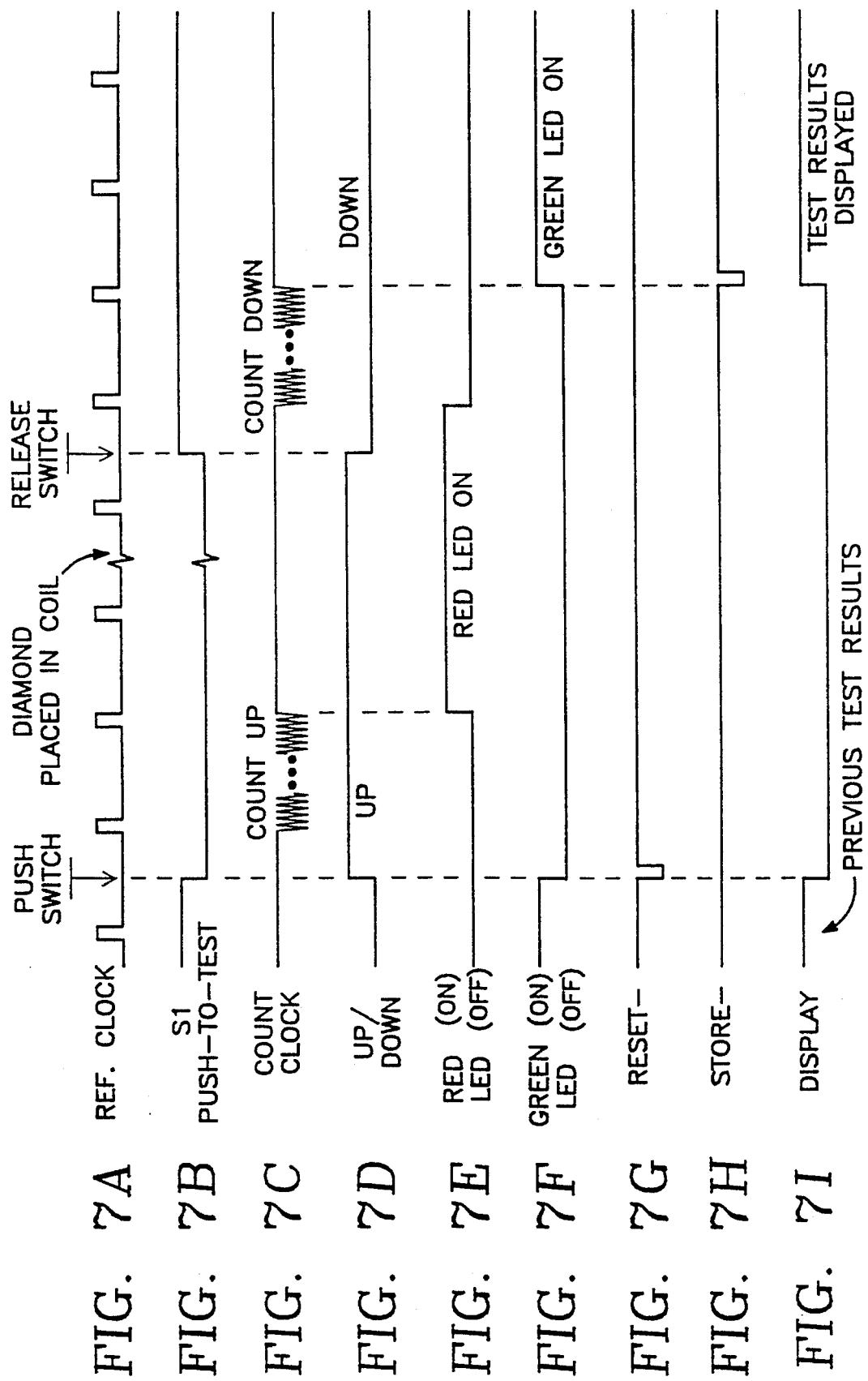
FIGS. 7A–7I is a set of timing signal graphs depicting the operation of the control logic and system of the detector of FIG. 1.
Figure 8:
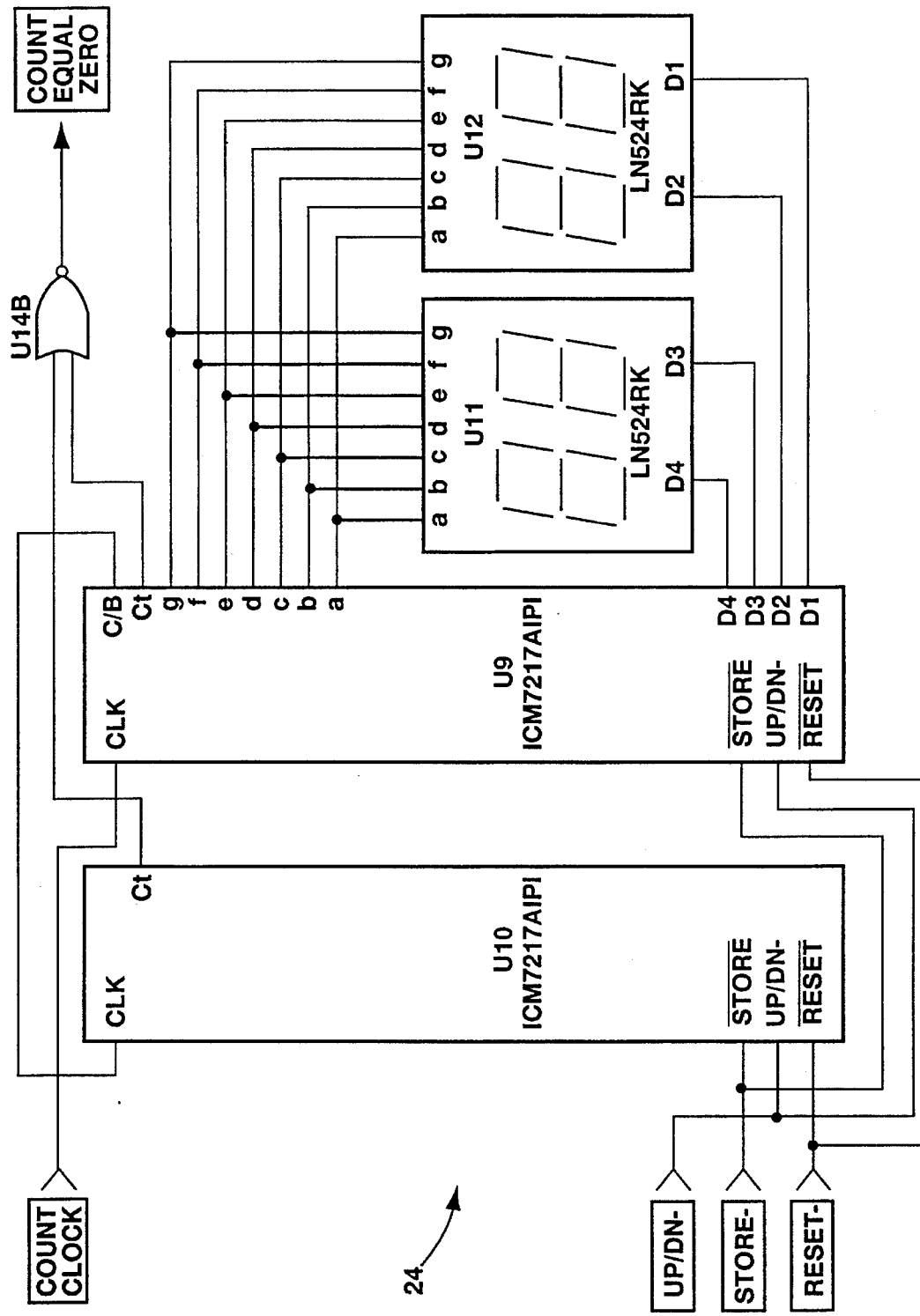
FIG. 8 is a detailed circuit diagram of the up/down counter and display circuits of FIG. 1.
Figure 9:
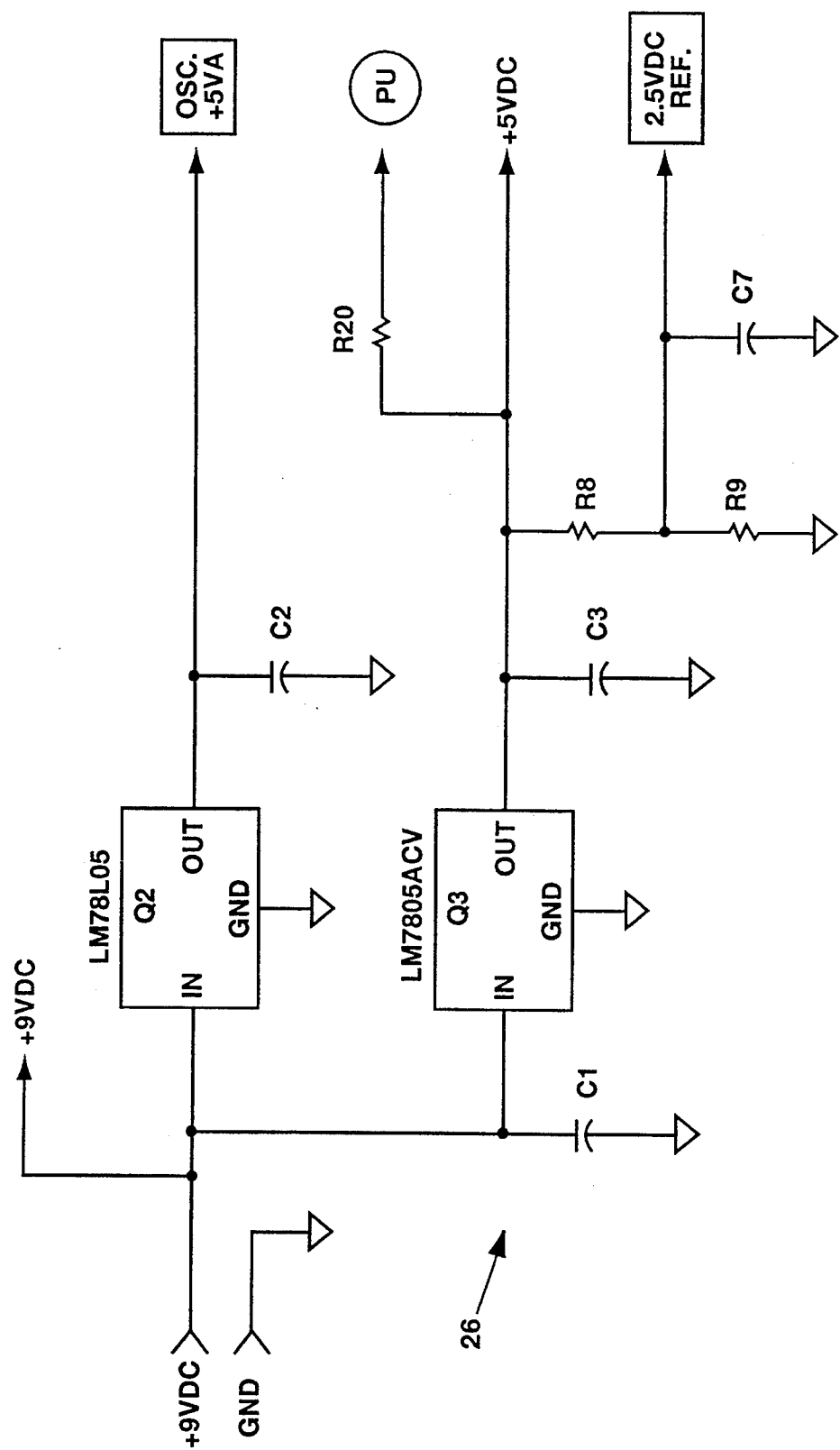
FIG. 9 is a detailed circuit diagram of the voltage regulator circuit of FIG. 1.

The control logic is shown in FIGS. 1 and 6 and consists of three sections, as follows: a reset circuit, a count-up circuit, and a count-down circuit.

The reset circuit consists of integrated circuits U8B, U5A, U14A, U1D, resistor R2 and capacitor C5. R2 and C5 set the pulse width of the RESET- and send the clear pulse to integrated circuits U3A and U7A. Whenever the count of the up/down counter equals zero or the push to test switch S1 is depressed (UP/DN—transitions to logic HI), U5A outputs the RESET—and the clear pulse.

The count up circuit consist of integrated circuits U1C, U3A, U3B, U15A, U15C, U1A, U13B, U7A, LED CR2-A and resistor R19. Integrated circuits U3A and U7B are cleared when the push to test switch is depressed (UP/DN—transitions to Logic High). The green LED is turned off at this time. On the next high to low transition of the REF clock, the OSC output is gated to the Count Clock by integrated circuit U15C, U1A and U13B. integrated circuit U3B is cleared at this time by integrated circuit U3A $\overline{Q}$ output starting the count up cycle. On the next low to high transition of the REF clock the OSC output is gated off at integrated circuit U13B output by integrated circuits U3B $\overline{Q}$, U15C and U1A. At this time integrated circuit U3B Q output clocks integrated circuit U7A turning on the red LED CR2-A indicating the up count or calibrate cycle is complete.

Count down circuit consist of integrated circuits U1C, U4A, U4B, U15B, U15D, U1B, U13B, U5B, U7B, LED CR2-B and resistor R18. Integrated circuits U4A and U7A are cleared when the push to test switch is released (UP/DN—transitions to logic LO). The red LED is turned off at this time. On the next HI to LO transition of the REF CLOCK the OSC OUTPUT is gated to the count clock by integrated circuit U15D, U1B and U13B. Integrated circuit U4B is cleared at this time by integrated circuit U4A $\overline{Q}$ output, starting the count down cycle. On the next LO to HI transition at the REF Clock the OSC output is gated off at integrated circuit U13B output by integrated circuit U4B $\overline{Q}$, U15D and U1B. At this time integrated circuit U4B Q output clocks integrated circuit U7B turning on the green LED CR2-B indicating the count down or measurement cycle is complete. Also at this time, integrated circuit U5B—TR input is clocked causing a STORE—pulse. Resistor R1 and capacitor C4 set the STORE—pulse width.

See FIG. 7A–7I for control logic and system timing graphs.

Up/Down Counter Display 24

Integrated circuits (integrated circuit) U9 and U10 form an eight digit LED display driver with programmable up/down counter. This counter is controlled by the following four inputs and two sets of outputs "RESET" This input when pulsed logic low will reset the counter to zero "STORE" This input when pulsed logic low will store the existing value of the counter and cause it to be displayed on the four digit display U11 and U12.

"UP/DN" This input when logic HI causes the counter to count up one count for each "COUNT CLOCK" cycle. When logic low the counter will count down.

"COUNT CLOCK" Each cycle of the count clock causes the count to count up or down one count depending on the state of "UP/DN".

"COUNT EQUAL ZERO" This output goes logic HI when the count of both integrated circuit U9 and U10 equal zero.

Display drive a,b,c,d,e,f,g,D1,D2,D3 and D4 drive LED display integrated circuit U11 and U12.

Voltage Regulator 26

The voltage regulator has two (2) +5 vDC regulator circuits. One for the sample oscillator circuit and one for the remainder of the diamond test circuit. The separate voltage regulator for the sample oscillator improves the sample oscillators stability.

Voltage regulator integrated circuit Q2 and capacitor C2 form the sample oscillator +5 vAC supply. Capacitor C2 stores energy and reduces ripple at the output of Q2.

Voltage regulator integrated circuit Q3 and capacitors C1 and C2 form the +5 vDC supply for the remainder of the detectors circuits. Capacitor C1 and C2 store energy and reduce supply ripple.

Resistor R20 output provides a logic HI pull up (PU) for the logic inputs that need to be a logic HI at all times. Resistor R8 and R9 form a resistive divider to produce a 2.5 vDC reference voltage. Capacitor C7 provides decoupling for the 2.5 vDC reference. A +9 vDC level is provided to the diamond detector by a standard UL approved regulated wall mount power supply.

System Operation

In summary, the diamond test has four operator interface indicators and controls. They are the push-to-test switch, 4 digit LED (should this not be liquid crystal) display, red and green LED indicators and the sample coil.

The sequence of operation of the diamond detector is as follows (after plugging in the +9 vDC wall mount power supply and allowing the detector approximately 5 minutes to warm-up):

The push-to-test switch 22 is pressed FIG. 7B) and held down. The green LED CR2-A will go out (FIG. 7F). After approximately 6 seconds the red LED CR2-B will illuminate (FIG. 7E) indicating the completion of the calibration cycle in which the count clock counts up the number of sample oscillator cycles (FIG. 7C) during the calibration interval (FIG. 7A).

2) The diamond to be tested is placed in the sample coil and the push-to-test switch is released FIG. 7B). The red LED will go out at this time FIG. 7E).

3) During the next available interval (FIG. 7A) the count clock recounts as a down-count the sample oscillator cycles (FIG. 7C). After approximately 6 seconds the green LED will illuminate (FIG. 7F) indicating completion of the measurement cycle and test. The STORE signal is given to the display circuits (FIG. 7H) and the results displayed (FIG. 7I). At this time the results of the test will be displayed on the four digit display.

It is found that stable oscillators will result in count differences between natural and synthetic stones of above about 25 counts for signals having total count values of about 2 million. This leads to the requirement that the counting circuits be stable over the testing process time to less than that value, preferably to about one (1) part per million for 5–10 seconds. Stability is easily checked, by the way, by performing the entire sequence without a sample stone in place. This should result in a count of less than 3 cycles.

As an example of the criteria for a synthetic stone identification in accordance with the present invention, for a sample oscillator frequency of 800 kHz, and a sampling interval of 4 seconds, it is expected that no natural stone will result in a count difference greater than 25 cycles. Any value greater than 25 cycles should be considered to be likely to have resulted from testing a synthetic diamond.

While the invention has been disclosed in a form for ready implementation in discrete logic circuits, it is to be understood that the reference oscillator, control logic circuits and counting circuits could readily be implemented on a computer chip with appropriate programming.

Figure 10:
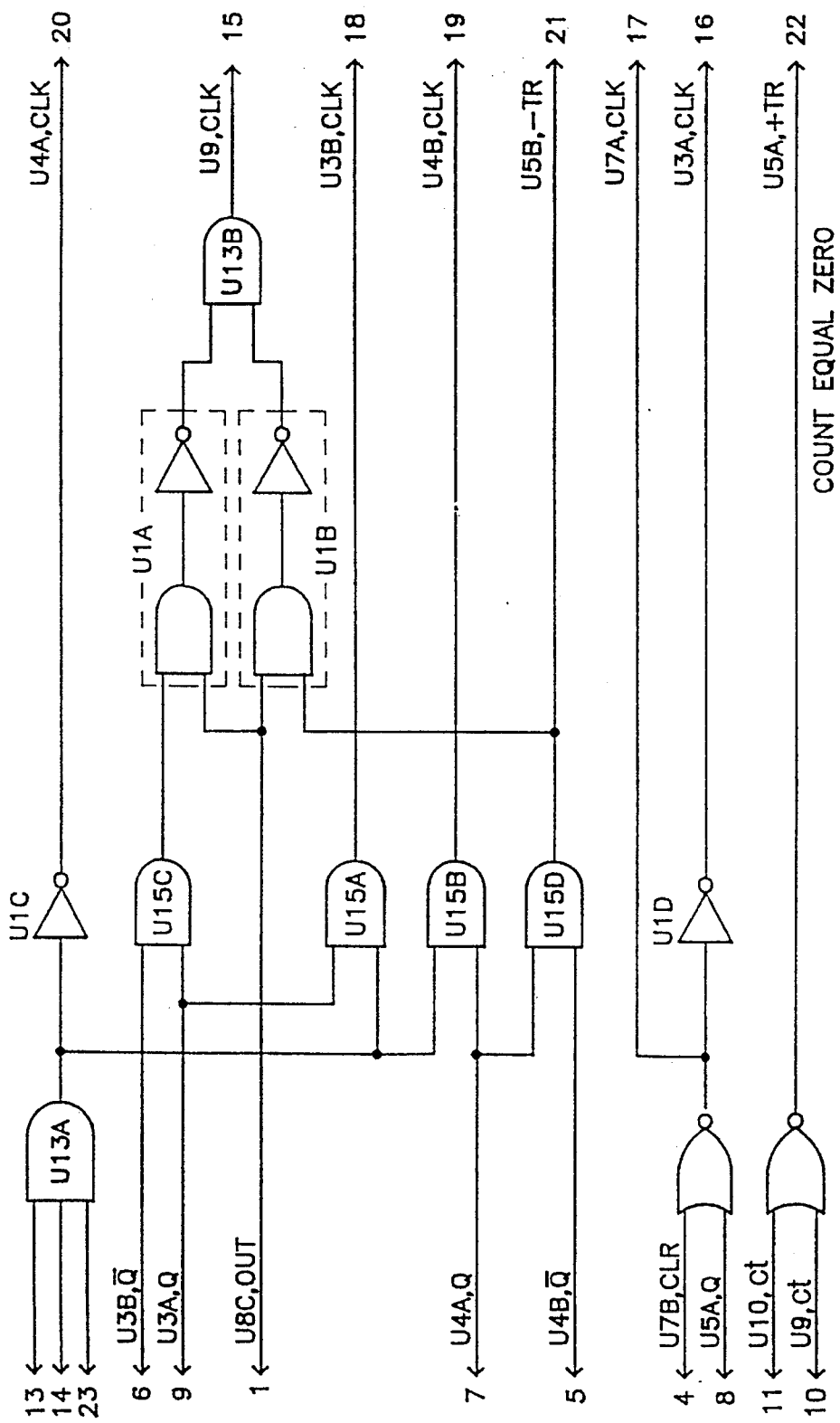
FIG. 10 is a logic diagram for programming a programmable logic device for use in an alternate embodiment of the invention.

By way of an example, and referring to FIG. 10, there is shown a logic diagram representing the logic circuit program for a 20V8 PLD (programmable logic device) chip. Such a PLD chip is provided with an internal logic gate block for realizing a logic circuit specified by the user in the form of a circuit configuration data written into a memory circuit. The form of circuit configuration is the logic circuit itself such as is shown in FIG. 10. After receiving the logic circuit configuration, the PLD chip performs in accordance with that logic. When so programmed according to the logic of FIG. 10, the 20V8 PLD chip can directly replace the entire circuit of FIG. 6. The 20V8 PLD pin assignments are given as arrowed references 1–23 in FIG. 10. The equivalent connections for substituting the chip into the previously described circuit of FIGS. 1–9 are given immediately over the respective leads, as U3A,Q . . . U10,Ct. It is not necessary to set forth the programming in detail as the logic configuration shown is used directly for programming the PLD chip. Such logic chips are available from Advanced Micro Devices of Sunnyvale, Calif. and from Monolithic Memories of Sunnyvale, Calif., among others. By using a programmable logic device the size and cost of the circuits is reduced.

To those skilled in the art to which the invention pertains many modifications and adaptations will occur. For example, while the oscillators and other circuits shown have been implemented with discrete components, they could readily be implemented on a programmable logic chip or chips as well.

Many other modifications and improvements will occur to those skilled in the art to which this invention pertains when utilizing the principles of this invention and all such improvements and modifications should be considered as within the scope of the present invention, and as comprehended within the scope of the following claims.

What is claimed is:

1. A method for distinguishing a synthetic diamond from a natural diamond by measuring a magnetic characteristic of a sample diamond, comprising:

providing an oscillator having a frequency determining inductor, said inductor being at least in part air-cored and having a port therein for admitting a sample diamond for testing, providing a counter for measuring counting transitions of said oscillator, up counting the oscillations over a precise time interval with no sample diamond present, then placing a sample diamond into said port of said inductor to change the frequency of said circuit by an amount related to the quantity of magnetic material in said sample diamond, down counting the oscillations with the sample diamond in place over a second time interval equal to said first interval, determining the difference in said counts, and displaying the difference in a digital readout as a measure of the magnetic content of said sample and the degree of likelihood of said sample being synthetic.

2. The method of claim 1 further including the preliminary step of calibrating the procedure by noting the difference counts of successive first and second intervals when performing the entire test cycle with no sample diamond present, and testing thereafter only if such difference calibration count is less than a predetermined value.

3. The method of claim 1 in which said sample oscillator frequency is selected to lie in the range of from about 100 kHz to 2 MHz.

4. The method of claim 1 in which said sample oscillator frequency is about 800 kHz.

5. The method of claim 1 in which said interval time value is about from 0.5 to 8 seconds.

6. The method of claim 1 in which said interval time value is about from 4 seconds.

7. A method for distinguishing synthetic diamonds from natural diamonds as in claim 1, further comprising:

providing a push-to-test switch to activate the counter for the first time interval when pressed and to reactivate the counter to repeat the count over the second time interval when pressed again or released, up counting the oscillations over the precise first time interval with no sample present by pressing said switch, then immediately placing a sample diamond into coupled proximity with said inductor to change the frequency of said circuit by an amount related to the quantity of ferromagnetic material in said sample diamond, pressing or releasing said switch again to begin down counting the oscillations with the sample diamond in place over the second time interval equal to said first interval, determining the difference in said counts, and displaying the difference in a digital readout as a measure of the degree of likelihood of said sample being synthetic.

8. Apparatus for distinguishing synthetic diamonds from natural diamonds by measuring the magnetic characteristic of a sample diamond, comprising:

an oscillator including an inductor for determining its frequency of operation, said inductor being at least in part air-cored and having a port therein for admitting a sample diamond for testing, a counter for measuring counting transitions of said oscillator, means for up counting the oscillations over a precise time interval with no sample present, after which a sample diamond to be tested is placed into said port of said inductor to change the oscillator frequency by the amount of magnetic material in said sample diamond, means for down counting the oscillations over a second time interval precisely equal to said first interval, means for determining the difference in said counts, and means for displaying the difference in a digital readout as a measure of the degree of likelihood of said sample being synthetic.

9. The apparatus of claim 8 in which said sample oscillator frequency is selected to lie in the range of from about 100 kHz to 2 MHz.

10. The apparatus of claim 8 in which said sample oscillator frequency is about 800 kHz.

11. The apparatus of claim 8 in which said interval time value is about from 0.5 to 8 seconds.

12. The apparatus of claim 8 in which said interval time value is about from 4 seconds.

13. The apparatus of claim 8 further including an operator control switch which starts up counting when actuated, an indicator circuit for showing the operator when up counting is complete, said control switch starting the down count when released by the operator after the indicator circuit is activated.

* * * * *